(12) United States Patent
Koyama et al.

(10) Patent No.: US 7,448,377 B2
(45) Date of Patent: Nov. 11, 2008

(54) INTUBATION ASSISTANCE INSTRUMENT AND INTUBATION ASSISTANCE APPARATUS PROVIDED WITH THE INTUBATION ASSISTANCE INSTRUMENT

(75) Inventors: Junichi Koyama, 2-3-28-2-102, Sawamura, Matsumoto-shi, Nagano 390-0877 (JP); Yukio Taniguchi, Saitama (JP)

(73) Assignees: HOYA Corporation, Tokyo (JP); Junichi Koyama, Nagano (JP)

( * ) Notice: Subject to any disclaimer, the term of this patent is extended or adjusted under 35 U.S.C. 154(b) by 469 days.

(21) Appl. No.: 11/235,157

(22) Filed: Sep. 27, 2005

(65) Prior Publication Data

US 2006/0065268 A1  Mar. 30, 2006

(30) Foreign Application Priority Data

Sep. 27, 2004  (JP) .............................. 2004-280529

(51) Int. Cl.
*A61M 11/00* (2006.01)
(52) U.S. Cl. ............................. 128/200.26; 128/207.14
(58) Field of Classification Search ............ 128/200.26, 128/207.14, 207.15, 207.16; 600/185, 188, 600/186, 194–199
See application file for complete search history.

(56) References Cited

U.S. PATENT DOCUMENTS

| 3,926,196 | A |  | 12/1975 | Bornhost et al. |
| 4,198,970 | A |  | 4/1980 | Luomanen |
| 4,256,099 | A |  | 3/1981 | Dryden |
| 4,363,320 | A |  | 12/1982 | Kossove |
| 5,203,320 | A | * | 4/1993 | Augustine .................... 600/187 |
| 6,543,447 | B2 | * | 4/2003 | Pacey ..................... 128/200.26 |
| 6,843,769 | B1 | * | 1/2005 | Gandarias ................... 600/189 |
| 7,156,091 | B2 | * | 1/2007 | Koyama et al. ......... 128/200.26 |
| 2005/0150500 | A1 |  | 7/2005 | Koyama et al. |

FOREIGN PATENT DOCUMENTS

| EP | 1598001 | 11/2005 |
| JP | 8-322937 | 12/1996 |
| WO | 2004-073510 | 9/2004 |

* cited by examiner

*Primary Examiner*—Steven O Douglas
(74) *Attorney, Agent, or Firm*—Greenblum & Bernstein, P.L.C.

(57) ABSTRACT

An intubation assistance instrument which is used by being inserted into the trachea of a patient through the mouth thereof includes an insertion section having a straight portion with a tip part and a curved portion continuously extended from the tip part of the straight portion. The insertion section is formed with a groove along a longitudinal direction thereof. The curved section has an inner wall part and an outer wall part which define the groove, and the outer wall part is formed with a cut out portion other than a tip part of the curved portion. The intubation assistance instrument and an intubation assistance apparatus provided with the instrument make it possible to carry out intubation operation with simple operation easily and safely.

15 Claims, 6 Drawing Sheets

INTUBATION ASSISTANCE INSTRUMENT AND INTUBATION ASSISTANCE APPARATUS PROVIDED WITH THE INTUBATION ASSISTANCE INSTRUMENT

BACKGROUND OF THE INVENTION

1. Field of the Invention

The present invention relates to an intubation assistance instrument for use in inserting a distal end of an intubation tube connected to an artificial ventilator into the trachea of a patient and an intubation assistance apparatus provided with the intubation assistance instrument.

2. Description of the Prior Art

In a case where a patient is suffering from unconsciousness or has lost consciousness because of an accident or the like, it is sometimes necessary to give rescue breathing as basic life support. Although it is possible to give rescue breathing without using any instrument or apparatus, a ventilator is used when necessary.

In the case where a ventilator is used, the distal end of an intubation tube of which proximal end is connected to the ventilator is inserted into the trachea of a patient to supply air to the trachea from the ventilator via the tube.

In the meantime, generally, when a patient is suffering from unconsciousness or has lost consciousness, the root of the tongue is retracted because of relaxation of the muscles of the pharynx and the larynx and/or loosening of the lower jaw due to the gravity, thereby blocking the airway.

Therefore, prior to the insertion of an intubation tube for rescue breathing into the trachea (hereinafter, this operation will be referred to as "intubation operation"), it is necessary to open such blocked airway to secure the passage of air.

As an instrument for use in securing the airway, an instrument referred to as an oral airway is known (one example thereof is disclosed in JP-A 8-322937).

Such an oral airway has an insertion section to be inserted through the mouth of a patient who is suffering from unconsciousness or has lost consciousness. By inserting the insertion section through the mouth of such a patient so that an appropriate portion located on the distal end side of the insertion section can come into contact with the root of the tongue of the patient, it is possible to widen or open the root of the tongue, thereby enabling the airway to be secured.

However, since the oral airway is used for only securing the airway, an operator cannot observe a site from the pharynx to the larynx (and the rima glottidis in the larynx) during the use thereof. This means that it is difficult for the operator to insert an intubation tube into the trachea of the patient in a state that such an oral airway is being used, since the operator can not observe the site.

On the other hand, a laryngoscope can also be mentioned as an instrument having the function of securing the airway. Such a laryngoscope includes an insertion section having a bar-like shape for use in securing the airway, image acquiring means provided on the distal end of the insertion section such as CCD or the like, and means for displaying an image taken by the image acquiring means such as a display.

The laryngoscope has both the functions of securing the airway and observing a site from the pharynx to the larynx.

Use of such a laryngoscope makes it possible to observe a site from the pharynx to the larynx when an operator inserts an intubation tube into the trachea of a patient. Therefore, insertion of the intubation tube into the trachea can be carried out easily to a certain extent. However, since the intubation tube to be inserted is made of a flexible material and the rima glottidis is narrow, insertion of such a tube through the rima glottidis into the trachea still requires specialized expertise.

As described above, the use of such conventional instruments still requires an operator to have specialized expertise for inserting a tube into the trachea of a patient.

SUMMARY OF THE INVENTION

It is therefore an object of the present invention to provide an intubation assistance instrument by which an intubation operation can be carried out easily and reliably with simple operation and higher safety, and an intubation assistance apparatus provided with the intubation assistance instrument.

In order to achieve the above-mentioned object, the present invention is directed to an intubation assistance instrument which is used by being inserted into the trachea of a patient through the mouth thereof. The intubation assistance instrument includes an insertion section having a straight portion with a tip part and a curved portion continuously extended from the tip part of the straight portion. The insertion section is formed with a groove along a longitudinal direction thereof. The curved section has an inner wall part and an outer wall part which define the groove, and the outer wall part is formed with a cut out portion other than a tip part of the curved portion.

According to the present invention described above, it is possible to provide an intubation assistance instrument which has a relatively small insertion section, and thus intubation operation of an intubation tube can be carried out easily and reliably with simple operation and higher safeness.

In the intubation assistance instrument described above, it is preferred that the tip part of the outer wall part is extended to a position distally far away from a tip part of the inner wall part. This makes it possible to direct the protruding direction of the intubation tube protruded from the groove to the rima glottidis of a patient easily and reliably.

Further, in the intubation assistance instrument described above, it is also preferred that the insertion section has a bottom which defines the groove having a tip part, an edge of the tip part of the bottom is formed to be inclined so that an outer wall side of the edge distally protrudes than an inner wall side thereof. This also makes it possible to direct the protruding direction of the intubation tube protruded from the groove to the rima glottidis of a patient easily and reliably.

Further, in the intubation assistance instrument described above, it is also preferred that the insertion section has a bottom which defines the groove, the maximum height of the tip part of the outer wall part with respect to the bottom of the insertion section being higher than the maximum height of the inner wall part. This makes it possible to hold the intubation tube reliably.

Further, in the intubation assistance instrument described above, it is also preferred that the cut out portion is formed so as to extend to a base end of the outer wall part of the curved portion, and the straight portion has a wall part extending from a tip end to a base end thereof, the wall part being continued from the cut out portion so that the height of the wall part is gradually increased from the tip end of the wall part toward the base end thereof. This makes it possible to hold the intubation tube more reliably.

Furthermore, in the intubation assistance instrument described above, it is also preferred that the tip part of the outer wall part of the curved portion has a portion where its height is gradually increased from the tip end of the cut out portion toward the distal end of the insertion section. According to the intubation assistance instrument described above, since the straight portion can hold the intubation tube to regulate the advancing direction of the tube, it is possible to guide the intubation tube to the curved portion reliably.

Furthermore, in the intubation assistance instrument described above, it is also preferred that the portion of the tip part of the outer wall part of the curved portion is formed into a shape having a rounded apex part when viewed from the side thereof. This makes it possible to carry out the intubation operation without injuring the trachea of a patient.

Furthermore, in the intubation assistance instrument described above, it is also preferred that the insertion section has a bottom which defines the groove, the bottom has a cross section having a substantially arc shape. This makes it possible to guide the intubation tube more reliably, and thus the intubation operation can be carried out easily.

Moreover, it is also preferred that the intubation assistance instrument described above further includes means for regulating the protruding direction of the intubation tube when the intubation tube inserted into the groove is allowed to protrude from the distal end of the insertion section. According to the structure described above, the intubation tube protrudes from the distal end of the insertion section with maintaining its curved form reliably, it is possible to direct the protruding direction of the intubation tube protruded from the groove to the rima glottidis of a patient more reliably.

Moreover, in the intubation assistance instrument described above, it is also preferred that the regulating means is provided with a protrusion formed on the inner surface of the outer wall part to protrude into the groove. This also makes it possible to direct the protruding direction of the intubation tube protruded from the groove to the rima glottidis of a patient more reliably.

Moreover, in the intubation assistance instrument described above, it is also preferred that the length of the cut out portion from its base end to the tip end is 50 to 95% of the entire length of the insertion section at the side of the outer wall part. This makes it possible to reduce the size of the intubation assistance instrument as well as to hold the intubation tube reliably.

Moreover, in the intubation assistance instrument described above, it is also preferred that the intubation assistance instrument has the functions of removably holding a curved intubation tube and guiding the intubation tube into the trachea of the patient. Namely, in the intubation assistance instrument described above, it is possible to remove the intubation assistance instrument, that is, the insertion section from the mouth of the patient in the state that the intubation tube is being inserted in the airway of the patient after completion of the intubation operation.

Another aspect of the present invention is directed to an intubation assistance apparatus provided with the intubation assistance instrument as described above. According to this invention, it is possible to provide an intubation assistance apparatus provided with an intubation assistance instrument which has a relatively small insertion section, and thus intubation operation of an intubation tube can be carried out easily and reliably with simple operation and higher safeness.

Preferably, the intubation assistance apparatus described above further includes a main body to which the intubation assistance instrument described above is removably mounted. According to this structure the intubation assistance instrument can be changed in each time of use, infection of a patient by bacterium can be prevented and thus it has higher safeness.

These and other objects, structures and results of the present invention will be apparent more clearly when the following detailed description of the preferred embodiments is considered taken in conjunction with the appended drawings.

DETAILED DESCRIPTION OF THE PREFERRED EMBODIMENT

Hereinbelow, a preferred embodiment of an intubation assistance instrument and an intubation assistance apparatus provided with the instrument according to the present invention will be described with reference to the accompanying drawings.

Figure 1:
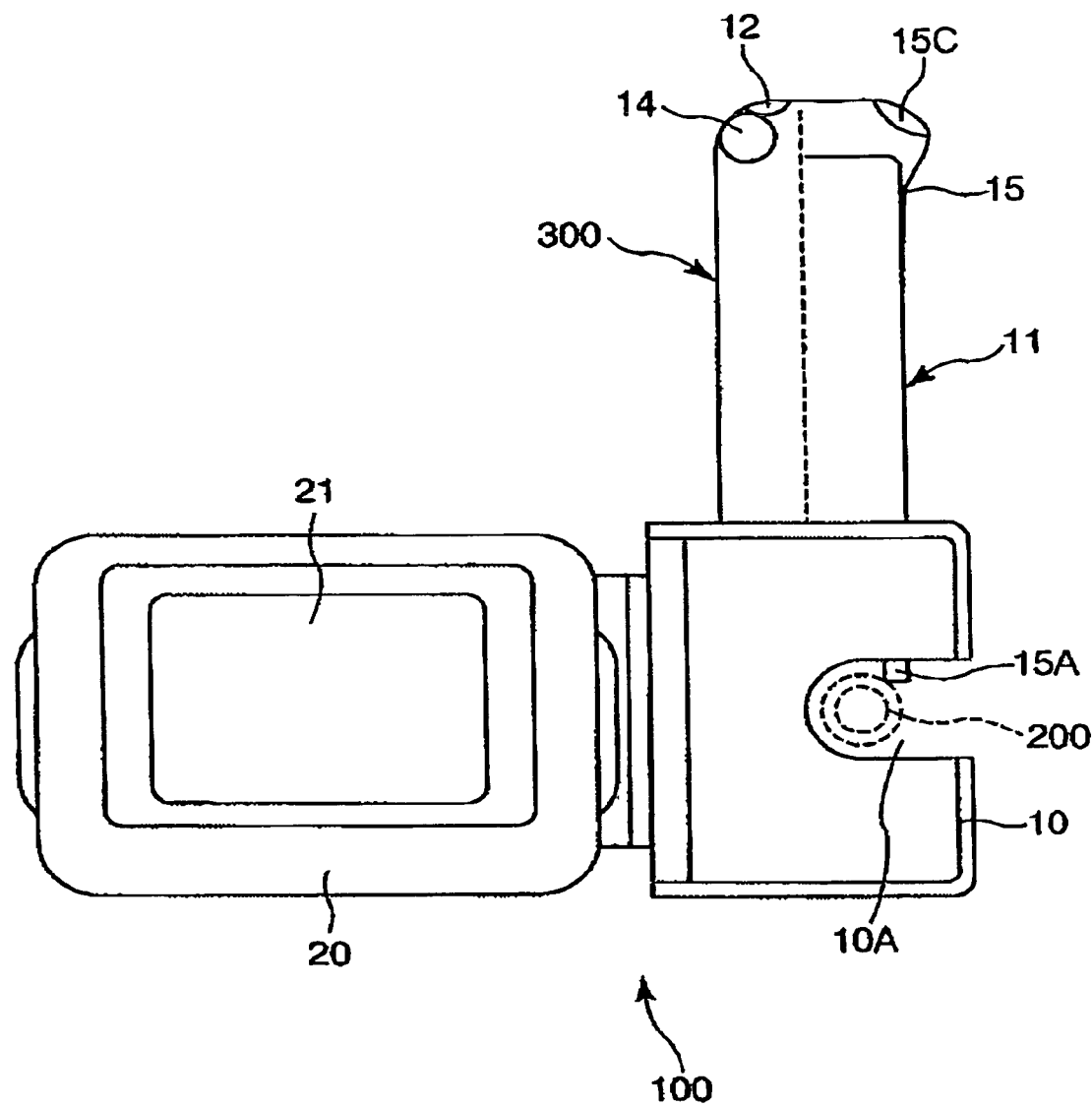
FIG. 1 is a rear view of the intubation assistance apparatus of the present invention.
Figure 2:
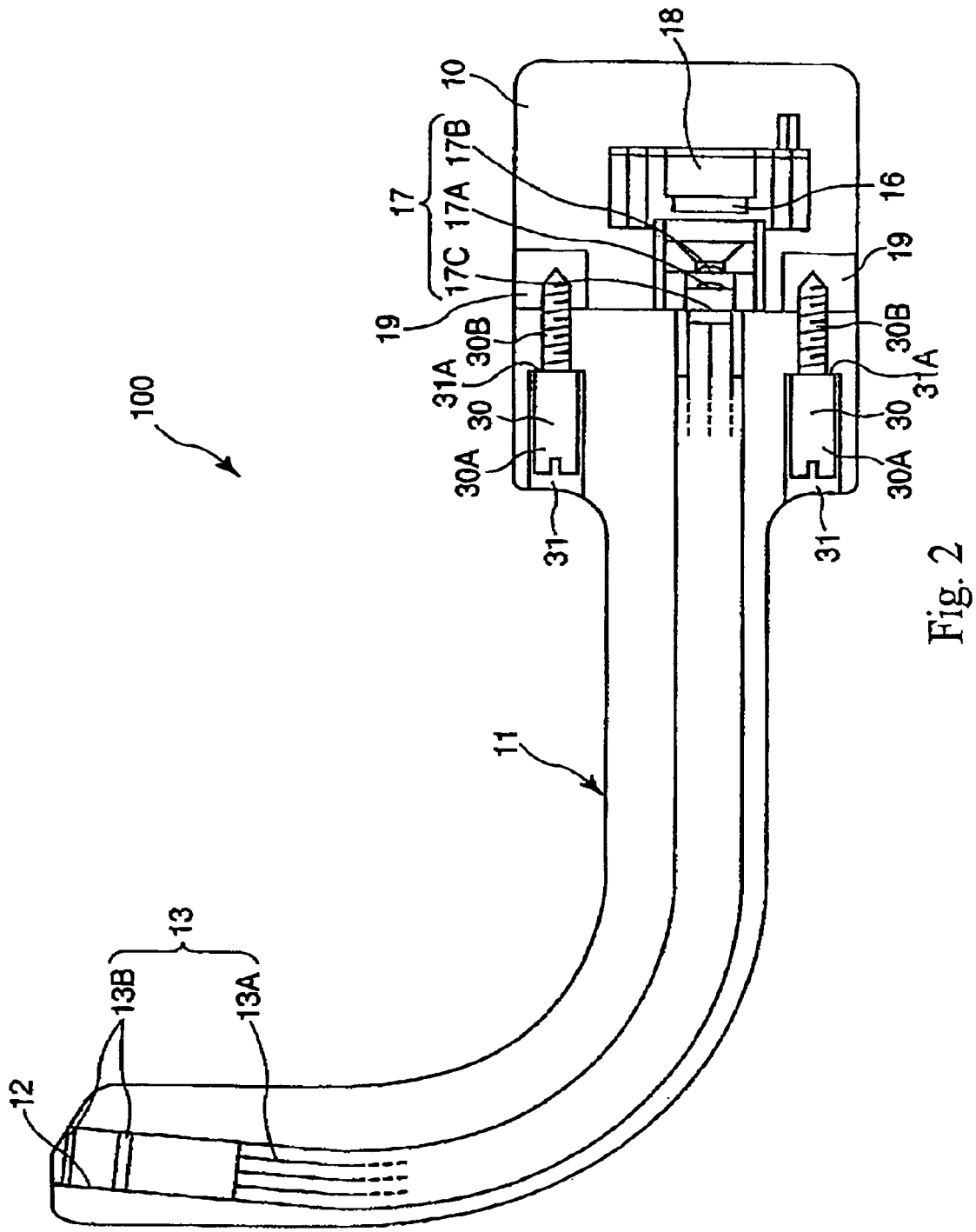
FIG. 2 is a side view of the intubation assistance apparatus shown in FIG. 1, which is shown in a fluoroscopic manner.
Figure 3:
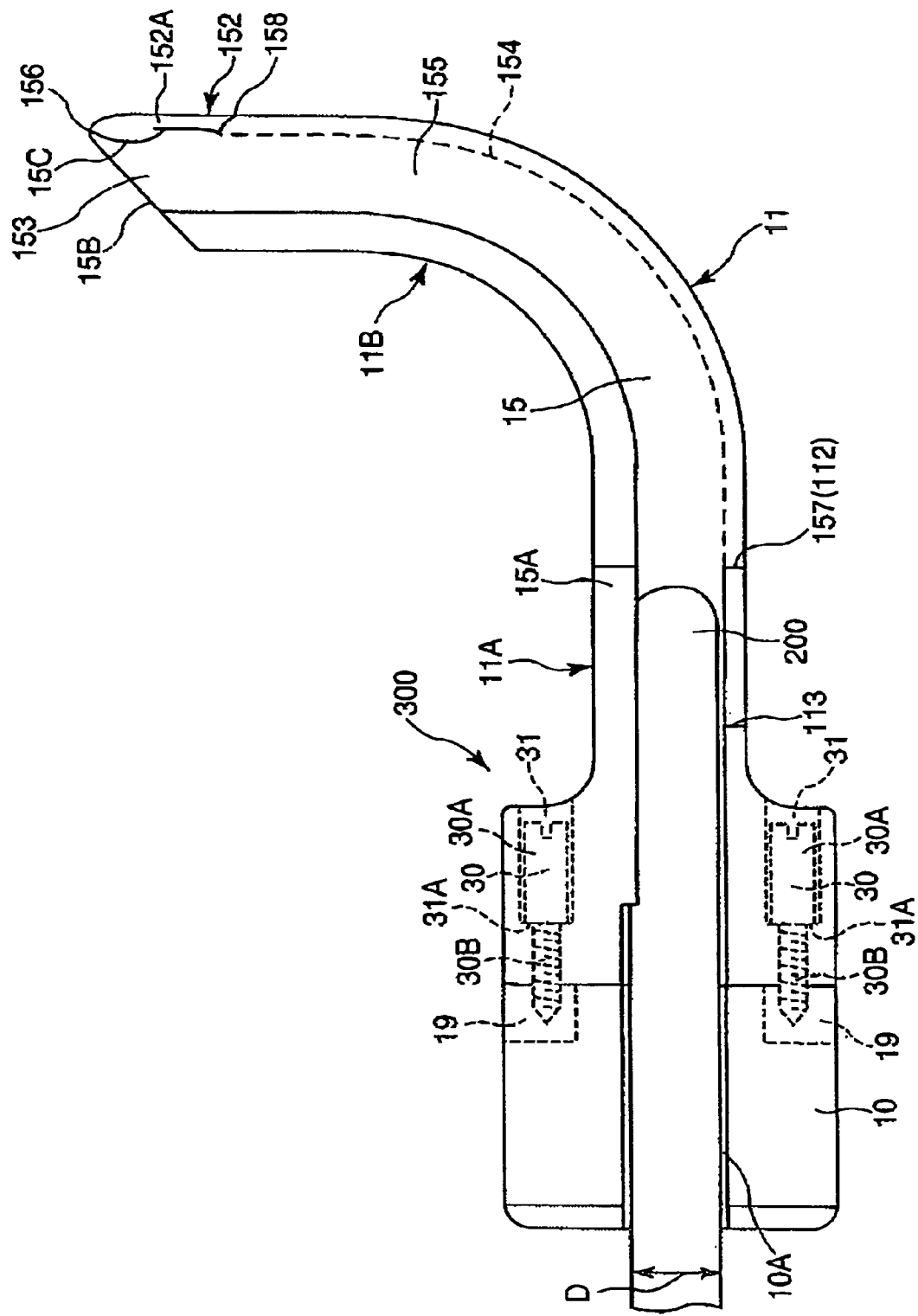
FIG. 3 is other side view of the intubation assistance apparatus shown in FIG. 1.
Figure 4:
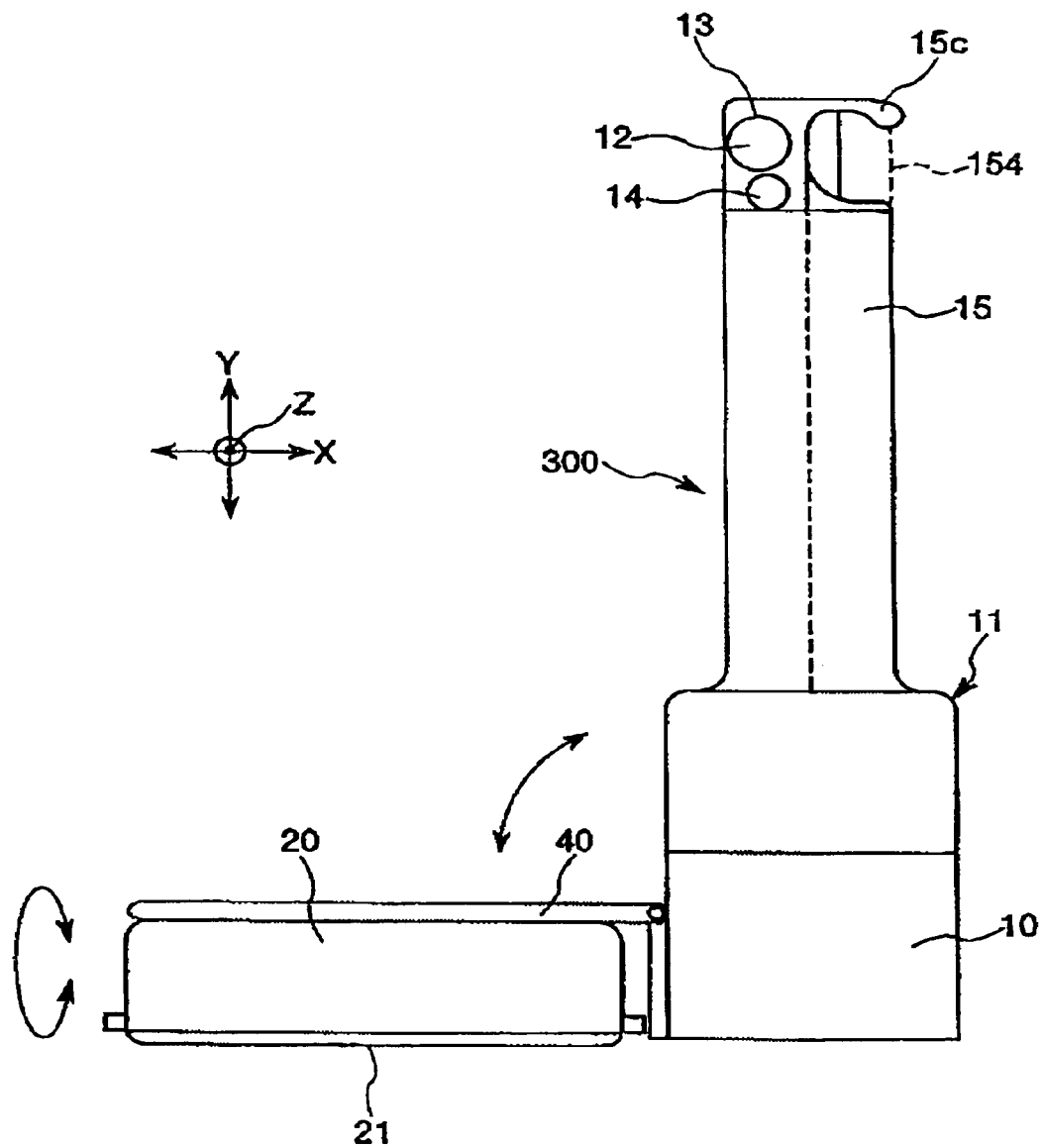
FIG. 4 is a plan view of the intubation assistance apparatus shown in FIG. 1.
Figure 5:
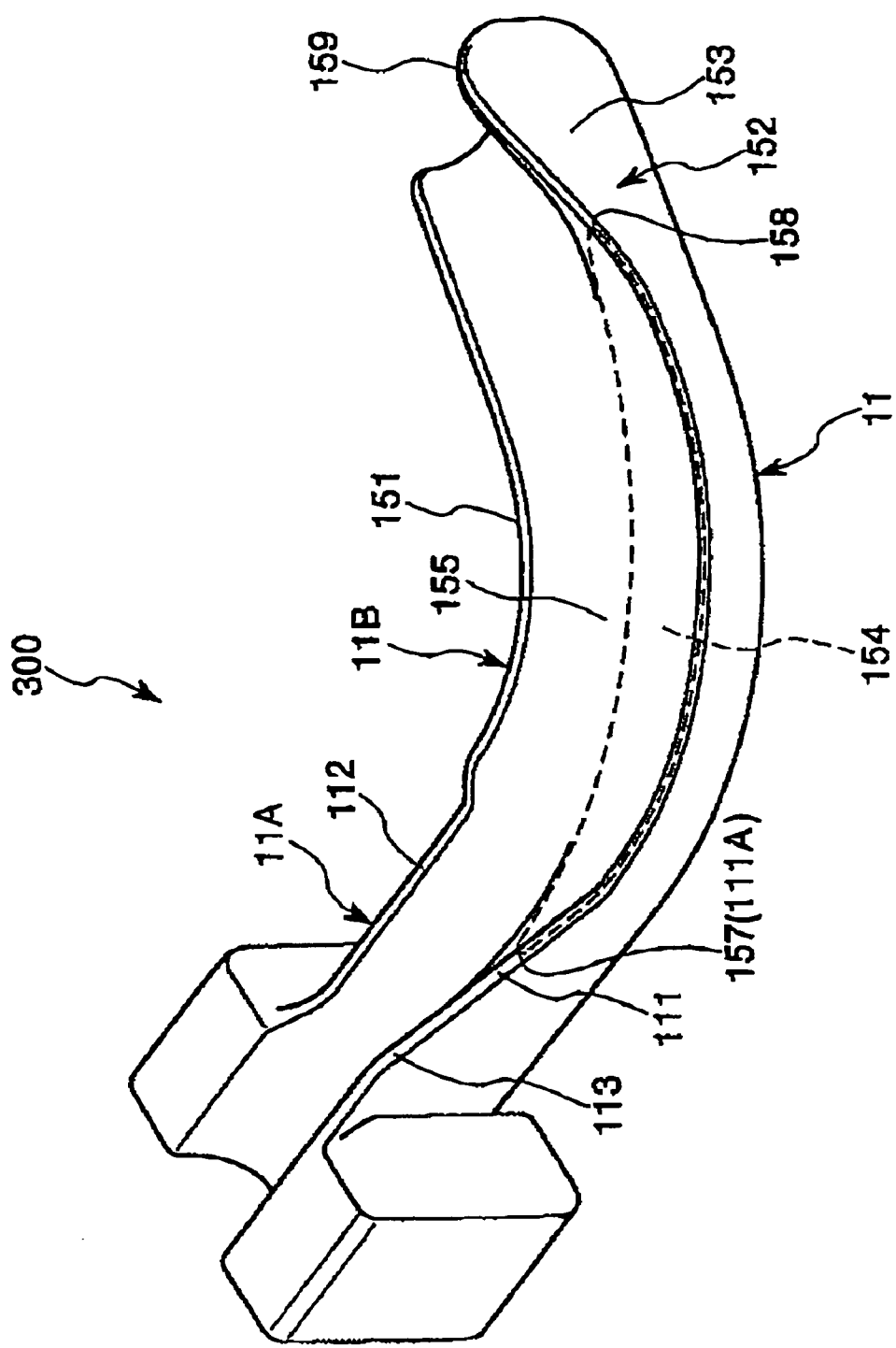
FIG. 5 is a perspective view which shown an embodiment of an intubation assistance instrument of the present invention.

FIG. 1 is a rear view of the intubation assistance apparatus of the present invention, FIG. 2 is a side view of the intubation assistance apparatus shown in FIG. 1, which is shown in a fluoroscopic manner, FIG. 3 is other side view of the intubation assistance apparatus shown in FIG. 1, FIG. 4 is a plan view of the intubation assistance apparatus shown in FIG. 1, and FIG. 5 is a perspective view which shows the embodiment of the intubation assistance instrument of the present invention.

In the following description, the upper side and the lower side in FIGS. 1 to 3 will be referred to as "upper" or "top" and "lower" or "bottom", respectively, the upper side and the lower side in FIG. 4 will be referred to as "front side" or "distal end" and "rear side" or "proximal end", respectively, the left side and the right side in FIGS. 1 and 4 will be referred to as "left side" and "right side", respectively, and the left side and the right side in FIG. 2 will be referred to as "front side" or "distal end" and "rear side" or "proximal end", respectively, and the right side and the left side in FIG. 3 will be referred to as "front side" or "distal end" and "rear side" or "proximal end", respectively, only for the purpose of clarity.

In addition, the left and right directions in FIG. 4 will be referred to as "X-axis direction", the up and down directions in FIG. 4 will be referred to as "Y-axis direction", and the perpendicular direction with respect to the X-axis direction and Y-axis direction will be referred to as "Z-axis direction", respectively.

The intubation assistance apparatus 100 shown in these drawings includes a main body 10 and an intubation assistance instrument 300 detachably mounted to the main body 10.

As will be described later in details the intubation assistance instrument 100 is used in combination with an intubation tube 200 which is to be inserted into the trachea of a patient through the mouth thereof.

As shown in FIG. 1, the intubation tube 200 has a substantially circular cross section and formed of an elastic material such as elastomer or rubber or the like.

The intubation assistance instrument 300 has an insertion section 11 which has the same function as that of an oral airway generally used, and such an intubation assistance instrument 300 is coupled to the main body 10.

The insertion section 11 is formed into an elongated member, and it is used for example by being inserted into the mouth of a patient who is suffering from unconsciousness or has lost consciousness. By inserting the insertion section 11 so that an appropriate portion located on the distal end side of the insertion part 11 comes into contact with the root of the tongue of a patient, it is possible to secure the airway of the patient.

As shown in FIGS. 2 and 3, the insertion section 11 includes a straight portion 11A and a curved portion 11B continuously extended from the tip side of the straight portion 11A and curved so that its tip side is curved upwardly.

In the present invention, the insertion section 11 is curved so that the tip side thereof is curved at a substantially 90° with respect to the base side thereof. Inside the insertion section 11, an image guide bore 12 is formed so as to extend from the proximal end to the distal end thereof.

The image guide bore 12 has a substantially circular cross section and an opening at the distal end of the insertion section 11.

As shown in FIG. 2, inside the image guide bore 12, an image guide 13 is provided.

The image guide 13 is composed from a bundle of optical fibers 13A and objective lenses 13B provided at the tip of the bundle of optical fibers 13A.

The image guide 13 receives reflected light from a site of observation at which the distal end of the insertion section 11 is positioned through the objective lenses 13B, and transmits an image of the observation site to a CCD (charge coupled device) 16 through the bundle of optical fibers 13A. In this way, the image guide 13 is capable of acquiring an image of at least the rima glottidis of a patient and its vicinity (the larynx including the rima glottidis of a patient) when the trachea of the patient is secured by the insertion section 11.

Namely, in the present invention, the image guide 13 constitutes means for transmitting an image of the observation site to the charge coupled device.

The bundle of optical fibers 13A is constructed from a plurality of optical fibers made of silica glass, multicomponent glass, plastic or the like.

Further, the insertion section 11 is formed with a light guide bore 14 arranged in a side by side relation with the image guide bore 12. The light guide bore 14 extends from the proximal end of the insertion section 11 to the distal end thereof.

The light guide bore 14 has an opening at the distal end of the insertion section 11. Inside the light guide bore 14, a light guide (not shown in the drawings) composed of a bundle of optical fibers is disposed.

The light guide introduces light from a light source (not shown in the drawing) which will be described later, and irradiate the observation site from the distal end of the insertion section 11. In this way, it is possible to irradiate the observation site where the distal end of the insertion section is positioned.

Namely, in this embodiment, the light guide constitutes means for transmitting light from the light source to the distal end of the insertion section 11.

In this connection, it is to be noted that the bundle of optical fibers which constitutes the light guide has the same structure as that of the bundle of optical fibers 13A.

As shown in FIG. 2, inside the main body 10, there is provided a CCD (charge coupled device) 16.

The CCD 16 is provided at a position that faces the proximal end of the image guide 13 in a state that the insertion section 11 is mounted to the main body 10. An image based on the light received by the distal end of the image guide 13 is formed on the CCD 16. That is, an image of the observation site where the distal end of the insertion section 11 is positioned is taken by the CCD 16.

Further, between the proximal end of the image guide 13 and the CCD 16, there is provided an optical enlargement system which includes two magnifiers 17A and 17B and an aperture 17C. Through this optical enlargement system, the image taken by the image guide 13 is formed on the CCD 16 in an enlarged manner. In this connection, it should be noted that the optical enlargement system is not limited thereto.

In this embodiment, the image guide 13, the CCD 16 and the enlargement optical system 17 constitute an image acquiring means for acquiring (taking) an image of the observation site where the distal end of the insertion section 11 is positioned.

In this connection, it is to be noted that instead of the CCD 16 the image acquiring means includes an eyepiece lens so as to be able to observe an observation site with naked eyes.

A display device 200 which includes a display 21 for displaying an image (image display means) is provided on the side of the main body 10 by means of a hinge 40.

The display 21 is formed from a liquid crystal display (LCD), an organic EL display, or the like, and it displays an image acquired by the image acquiring means.

As shown in FIG. 4, the hinge 40 is rotatably supported on the main body 10 about an X-axis. As s result, the display device 20 is rotatable about not only the Z-axis but also the X-axis.

Since the display device 20 is displaceable with respect to the main body 10 as described above, it is possible to direct the display device 20 to any desired direction in spite of the direction of the insertion section 11. Accordingly, it is possible to carry out the intubation operation safely and reliably irrespective of the body posture of a patient.

Further, inside the main body 10, there is also provided a controller 18 for displaying the image on the display device 20.

Under the control of the controller 18, the display device 20 displays the image taken by the CCD 16 on the display 21.

The image to be displayed on the display device 20 is an image including an image of the rima glottidis of a patient while the airway is being kept open by the insertion section 11.

Furthermore, inside the main body 10, there are also provided a light source constructed from a light emitting element such as LED or the like and a battery (not shown in the drawings).

The buttery supplies electrical power to the LED so that the LED emits light in response to the operation of a switch (not shown in the drawings) by an operator. The light emitted is transmitted to the distal end of the insertion section 11 through the light guide 13.

In this embodiment, the light guide 13 and the LED (light source) constitute an illumination means for illuminating an observation site where the distal end of the insertion section 11 is to be placed.

On the right side surface of the insertion section 11, a groove 15 (guide means) is formed from the proximal end of the insertion section 11 to the distal end thereof, that is, along the longitudinal direction of the straight part 11A and the curved part 11B of the insertion section 11.

The groove 15 has the function of guiding the intubation tube 200 to insert it from the mouth of a patient into the trachea of the patient in a state that the oral airway of the patient is being secured by the insertion section 11.

Further, on the right side surface of the main body 10, a groove 10A is formed at a position corresponding to the groove 15 in a state that the insertion section 11 is mounted to the main body 10. Due to this structure, it is possible to insert the intubation tube 200 into the groove 15 through the groove 10A.

When the oral airway of the patient has been secured by the insertion section 11, the intubation tube 200 is introduced into the groove 15, and then advanced toward the distal end of the insertion section 11. At that time, the intubation tube 200 is guided along wall parts 111, 112 of the straight portion 11A and then an inner wall part 151 and an outer wall part 152 of the curved portion 11B to advance in the groove 15 in a sliding manner. By further advancing the intubation tube 200 along the groove, the distal end of the intubation tube 200 protrudes from the distal end of the insertion section 11 toward the rima glottides of the patient positioned back of the larynx.

As stated in the above, the curved section 11B has the inner wall part 151 and the outer wall part 152 which respectively define a curved inner side of the groove 15 and a curved outer side of the groove 15. Further, the outer wall part 152 is formed with a cut out portion 154 where a portion of the outer wall part 152 other than a tip portion 153 of the curved portion 11B is cut out. Namely, the curved portion 11B is provided with the inner wall part 151 and the outer wall tip portion 152A which are minimally required structures for guiding the intubation tube 200.

In this embodiment, the cut out portion 154 is formed from the base end 157 of the curved portion 11B to the base end 158 of the outer wall tip portion 152A. That is, the base end 157 is a base part of the cut out portion 154 and the base end 158 is a tip pat of the cut out portion 154.

As shown in FIG. 5, the outer wall tip portion 152A has an apex part 150 which is the highest part of the outer wall part 152. The apex part 150 has a rounded shape when viewed from the side thereof (when viewed from the front side to the rear side in FIG. 3).

Further, the straight portion 11A has a wall part 111 which is continued from the cut out portion 154 and an wall part 112 which is continued from the inner wall part 151.

The height of the wall part 111 is gradually increased from the tip end 111A (corresponding to the base end 157 of the curved portion 11B) toward the base end 113. On the other hand, the height of the wall part 112 from the base end to the tip end thereof is lower than the height the inner wall part 151 and has substantially the same height.

In this regard, it is preferred that the length of the cut out portion 154 from the base end (the base end 157) to the tip end (the base end 158) is 50 to 90% of the length of the curved outer part of the curved portion 11B in the longitudinal direction, and more preferably 80 to 90% thereof. This makes it possible to reduce the size of the intubation assistance instrument 300 and also to guide and hold the intubation tube 200 reliably. Further the height of the cut out portion 154 (that is, the length of a portion of the out wall part 152 that has been cut out for forming the cut out portion 154) is preferably set to be 5 to 100% of the height between the bottom 155 and the imaginary line in FIG. 3 which hypothetically shows the upper edge of the outer wall part 152 when no cut out portion 154 would be formed, and more preferably set to be 50 to 90% of the height between the bottom 155 and the imaginary line in FIG. 3. When the height of the cut out portion 154 is set to a value close to 100% of the height between the bottom and the imaginary line, less wall part remains in the outer wall part 152. In such a case, the intubation assistance instrument 300 is used, that is inserted into the mouth of a patient, in a state that the insertion tube 200 is in advance set to the insertion section 11 (that is, in a state that the intubation tube 200 is being held by the distal end and the proximal end of the insertion section 11.

Further, the outer wall tip portion 152A of the outer wall part 152 is extended to a position distally far away from the tip part of the inner wall part 151 (upper side in FIG. 3).

As shown in FIG. 5, the inner wall part 151 has substantially the same height with respect to the bottom 155 along its entire length. Further, the height of the apex part 159 with respect to the bottom 155 is higher than the height of the inner wall part 151 with respect to the bottom 155. Furthermore, the bottom 15 is formed so as to have a substantially arc shape in its cross section.

The tip end of the bottom 155 of the groove 15 is formed with a notch 15B which is inclined so that the outer wall side protrudes distally (upwardly in FIG. 3) rather than the inner wall side thereof with respect the central axis of the groove 15. The intubation tube 200 is advanced through the notch 15B toward the rima glottides of the patient positioned back of the larynx.

On the inner surface of the outer wall part 152 which faces the notch 15B (that is, on the tip part of the insertion section 11 in this embodiment), there is formed a protrusion (regulating means) 15C which protrudes toward the groove 15. According to this structure, when the intubation tube 200 guided by the inner wall part 151 and the outer wall tip portion 152A reaches the protrusion 15C, the advancing direction of the intubation tube 200 is regulated so that the intubation tube 200 is directed toward the rima glottides of the patient more reliably.

As shown in FIG. 2 and FIG. 3, the intubation assistance instrument 300 described above is detachably mounted or fixed to the main body 10 with a plurality of screws 30. In this embodiment, the intubation assistance instrument 300 is mounted to the main body 10 through four screws 400 which include two sets of upper and lower screws provided on the left and right sides, respectively.

Further, as shown in FIG. 3, on the base end of the intubation assistance instrument 300, there are formed through holes 31 into which the screws 30 are threaded. Further, in the inside of each through hole 31, there is formed a step portion (a reduced diameter portion) which functions as a seat for the head of the screw 30.

When each screw 30 is threaded into the through hole 31, a male thread portion 30B of the screw 30 protrudes from the base end surface of the intubation assistance instrument 300. The protruded male thread portion 30B is threaded into a female thread portion 19B formed in the front surface (front end surface) of the main body 10 until the screw head 30A abuts onto the step portion 31A of the screw hole 31. In this way, the intubation assistance instrument 300 is fixedly mounted to the main body 10. On the other hand, the intubation assistance instrument 300 can be removed or detached from the main body 10 by loosening the screws 30 and then removing it, if necessary.

Further, in this embodiment, the screw head 30A of each screw 30 does not protrude from the opening of the through hole 31 in a state that the intubation assistance instrument 300 is mounted to the main body 10. This makes it possible to prevent the screws 30 from being loosened by attaching the screw heads 30A with a finger of an operator during the intubation operation and thereby the intubation assistance instrument 300 is accidentally removed or detached from the main body 10.

Furthermore, each of the screws 30 is threaded using a specific gig. This also makes it possible to prevent the intubation assistance instrument 300 is accidentally removed or detached from the main body 10.

In this connection, it should be understood that the method for mounting the intubation assistance instrument 300 to the main body 10 is not limited to the above method suing the screws 30. Other methods such as a method using a latchet mechanism, a screw mount method, and a bayonet mount method and the like may be used.

Since the intubation assistance instrument 300 is configured so as to be removable with respect to the main body 10, it is possible to change the intubation assistance instrument 300 upon every time of use. This makes it possible to prevent infection (secondary infection) of a patient by bacterium or the like, thus realizing high safeness.

Further, the removed intubation assistance instrument 300 may be repeatedly used after it is washed, disinfected and sterilized, but it is preferred such a device is configured as a disposable type. This makes it possible to prevent the secondary infection more reliably.

Hereinbelow, one example of the using method (operation) of the intubation assistance apparatus 100 will be explained.

The intubation assistance apparatus 100 is used for a patient loosing its consciousness and thereby it becomes necessary to insert an intubation tube 200 into the airway of the patient. In this regard, it should be understood that in this embodiment the intubation tube 200 is formed so as to have a curved form in advance.

(1) First, when the intubation tube 200 is to be inserted, the intubation assistance instrument 300 is mounted to the main body 10 with the screws 30.

(2) Then, the insertion section 11 of the intubation assistance instrument 300 is inserted into the airway of a patient through the mouth thereof.

More specifically, the insertion section 11 is inserted into the mouth of the patient so that the inside of the curved portion is kept in contact with the root of the tongue of the patient, thereby securing the airway.

(3) Next, after the airway of the patient has been secured by the distal end of the insertion section 11, the switch is operated to emit the LED. Light emitted from the LED is introduced into the light guide 13, and then emitted from the distal end of the insertion section 11 to irradiate the rima glottidis of the patient and its vicinity to light up that site.

The light reflected from the rima glottidis of the patient and its vicinity (that is, an image of the observation site) is captured by the objective lenses 13B, and it is then transmitted to the CCD 16 through the bundle of optical fibers 13A and the enlargement optical system 17. In this way, an image of the rima glottidis of the patient and its vicinity is formed on the CCD 16.

(4) Then, the image data taken by the CCD 16 is sent to the display device 20 through the controller 18, and the image of the rima glottidis of the patient and its vicinity is displayed on the display 21.

(5) Next, the intubation tube 200 is inserted into the groove 15 through the groove 10A. Then, by pushing the intubation tube 200, the intubation tube 200 is advanced in the groove 15 of the straight portion 11A with slidably contacting with the wall parts 111, 112. When the distal end of the intubation tube 200 reaches the inner wall part 151 of the curved portion 11B, the intubation tube 200 is advanced with slidably contacting with the inner wall part 151.

When the intubation tube 200 is further advanced, the distal end of the intubation tube 200 reaches the outer wall tip portion 152A. At that time, the distal end of the intubation tube 200 abuts on the protrusion 15C and thereby it is directed to the side of the upper side wall of the groove 15 and then it protrudes from the distal end of the insertion section 11 through the notch 15B with maintaining its curved form.

At that time, with monitoring the image (including the image of the distal end of the intubation tube 200) displayed on the display device 20, the intubation tube 200 is further advanced so that the distal end thereof is inserted into the rima glottidis of the patient to reach the trachea of the patient.

As stated in the above, the notch 15B is provided at a position through which the distal end of the intubation tube 200 is automatically directed to the rima glottidis of the patient. Therefore, it is relatively easy to direct the distal end of the intubation tube 200 toward the rima glottidis of the patient.

As described above, according to the intubation assistance apparatus of the present invention, since the intubation tube 200 can be inserted into the airway of the patient through the rima glottidis thereof with monitoring the image displayed on the display 21, and since the distal end of the intubation tube 200 is automatically guided into the rima glottides due to the provisions of the protrusion 15C and the notch 15B, the intubation operation of the intubation tube 200 into the airway can be carried out easily and reliably.

(6) Next, in the state that the intubation tube 200 is being inserted in the airway, the intubation tube 200 is deformed to remove it from the groove 15.

(7) Then, with maintaining this state, the insertion section 11 is removed from the mouth of the patient.

Through the above processes, it is possible to intubate the intubation tube 200 into the airway of the patient.

As described above, according to the intubation assistance apparatus 100, since the outer wall part of the curved portion 11B of the insertion section 11 is formed with the cut out portion 154, it is possible to reduce the size of the intubation assistance instrument 300, thereby enabling to improve operability and thus carry out the intubation operation of the intubation tube 200 easily and reliably.

Further, since the intubation tube 200 is held by the groove 15 removably or separately, it is possible to remove the intubation assistance instrument 300 (that is, the insertion section 11) from the mouth of the patient in the state that the intubation tube 200 is being inserted in the airway of the patient after completion of the intubation operation.

Furthermore, since the intubation assistance instrument 300 is configured so as to be removable or detachable to the main body 10, it is possible to change the intubation assistance instrument 300 upon every time of use. This makes it possible to prevent infection (secondary infection) of a patient by bacterium or the like, thus realizing high safeness.

Moreover, according to the intubation assistance apparatus 100 of the present invention, it is possible to shorten the time necessary for the intubation operation and thereby to reduce burden on the patient.

Moreover, since the intubation assistance apparatus 100 is provided with the image acquiring means and the illumination means, the operator can observe the pharynx and the larynx of a patient to grapes of the positional relation between the rima glottidis which is an entrance of the airway and the distal end of the intubation tube 200, thereby enabling the intubation operation to be carried out more easily and reliably.

Further, since the intubation tube 200 introduced into the groove 15 is held reliably by the inner wall part 151 and the outer wall tip portion 152A, it is possible to prevent the tube 200 from being removed from the open side of the curved portion 11B, so that the intubation tube 200 is guided safely and smoothly. In addition, by deforming the intubation tube 200, it is possible to remove or separate the intubation tube 200 from the groove 15 easily. This also contributes to carrying out the intubation operation easily.

Furthermore, since the intubation assistance apparatus 100 is provided with the CCD 16 and the LED in the main body 10, the structure of the intubation assistance instrument 100 can be made simple. This makes it possible to reduce the manufacturing cost of the intubation assistance instrument 100, and such a reduced manufacturing cost makes it possible to configure the intubation assistance instrument 300 as a disposable type.

The above described intubation assistance apparatus 100 may be provided with an indicator which indicates the remaining battery level in the main body 10. This makes it possible to prevent the intubation operation from being stopped during the operation due to the empty of the battery level.

Furthermore, the main body 10 may be provided with an output terminal for outputting the image data. This makes it possible to confirm the image of the observation site taken by the image acquiring means with a large external monitor larger than the display 21.

Moreover, in general, the proximal end of the intubation tube 200 is connected to an artificial ventilator to send air to the airway of a patient from the ventilator through the intubation tube 200 inserted into the airway through the rima glottidis of the patient. In this regard, it is to be noted that the connection between the proximal end of the intubation tube 200 and the ventilator may be carried out before or after the insertion of the intubation tube 200 into the airway of the patient.

Figure 6:
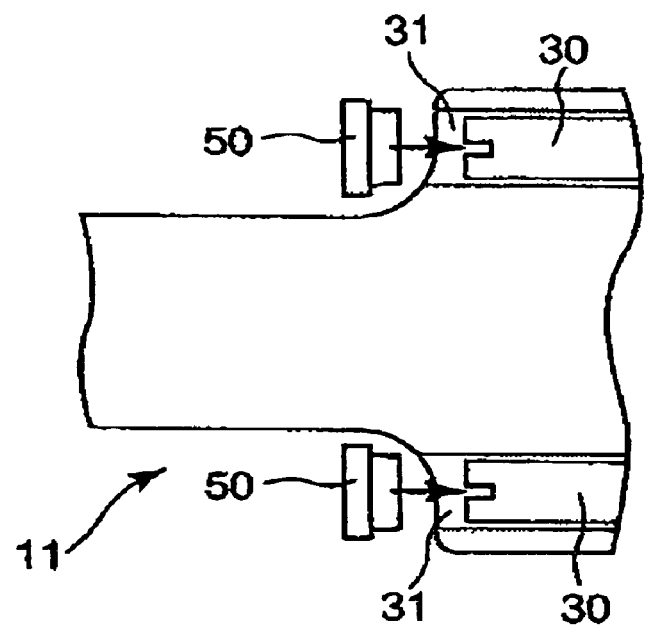
FIG. 6 is an illustration which shows elastic caps used in the intubation assistance instrument of the present invention.

Further, as shown in FIG. 6, the intubation assistance apparatus 100 of the present invention may be provided with elastic caps 50 for closing and sealing the openings of the through holes 31. These caps 50 are attached to the openings 31 in a state that the intubation assistance instrument 100 is mounted to the main body 10. This makes it possible to prevent a liquid such as a body fluid from entering into the inside of the main body 10 through the through holes 31 to avoid troubles of the intubation assistance apparatus 100. Such elastic caps 50 may be formed of a material such as various elastomers or various rubbers or the like.

Figure 7:
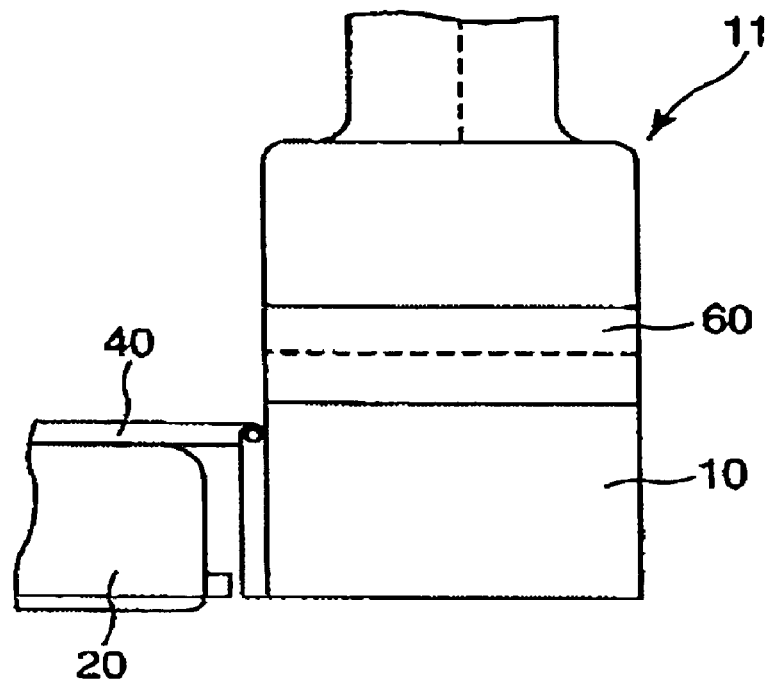
FIG. 7 is an illustration which shows the structure of a seal used in the intubation assistance instrument of the present invention.

Furthermore, as shown in FIG. 7, a seal member 60 may be provided between the intubation assistance instrument 300 and the main body 10. This also makes it possible to prevent a liquid such as a body fluid from entering into the inside of the main body 10 through the boundary part between the intubation assistance instrument 300 and the main body 10 to avoid troubles of the intubation assistance apparatus 100. Such a seal member 60 may be formed of a pressure sensitive adhesive tape or a thermally shrinkable tube or the like.

In the foregoing, an explanation has been made with regard to the embodiment of the intubation assistance instrument and the intubation assistance apparatus according to the present invention based on the accompanying drawings. However, the present invention is not limited thereto, and each component or element of the intubation assistance apparatus 100 may be replaced with other component or element that exhibits the same or similar function. Further, arbitrary components or structures may be added thereto.

For example, in the above described intubation assistance apparatus 100, the image of the observation site taken by the CCD 16 is displayed on the display 21. However, the main body 10 may be provided with a storage device such as a memory for storing the image data. By providing such a storage device, it will be possible to reconfirm the process of the intubation operation of the intubation tube 200 later.

Further, the main body 10 may be provided with an electronic data transmission device for transmitting the image data to a hospital to which the patient is to be sent through a telecommunications network. This makes it possible for the hospital to prepare medical attendance suitable for the patient during the transportation of the patient by an ambulance car.

Furthermore, in the above embodiment, the intubation assistance instrument 300 is detachably mounted to the main body 10. However, the intubation assistance instrument 300 may be fixedly mounted to the main body 10.

Finally, it is also to be understood that the present disclosure relates to subject matter contained in Japanese Patent Application No. 2004-280529 (filed on Sep. 27, 2004) which is expressly incorporated herein by reference in its entirety.

What is claimed is:

1. An intubation assistance instrument which is insertable into a trachea of a patient, the intubation assistance instrument comprising:
an insertion section having a straight portion with a tip part and a curved portion continuously extended from the tip part of the straight portion, the insertion section being formed with a groove along a longitudinal direction thereof, the curved portion having an inner wall part and an outer wall part which define the groove, and the outer wall part being formed with a cut out portion excluding a tip part of the curved portion, and wherein a tip part of the outer wall part is extended to a position distally away from a tip part of the inner wall part.

2. The intubation assistance instrument as claimed in claim 1, wherein the insertion section has a bottom which defines a bottom surface of the groove, the bottom having a tip part, wherein an edge of the tip part of the bottom is formed to be inclined so that an outer wall side of the edge distally protrudes farther than an inner wall side thereof.

3. The intubation assistance instrument as claimed in claim 1, wherein the insertion section has a bottom which defines a bottom surface of the groove, a maximum height of the tip part of the outer wall part with respect to the bottom of the insertion section being higher than a maximum height of the inner wall part.

4. The intubation assistance instrument as claimed in claim 1, wherein the cut out portion is formed so as to extend to a base end of the outer wall part of the curved portion, and the straight portion has a wall part extending from a tip end to a base end thereof, the wall part being continued from the cut out portion so that the height of the wall part is gradually increased from the tip end of the wall part toward the base end thereof.

5. The intubation assistance instrument as claimed in claim 1, wherein the tip part of the outer wall part of the curved portion has a portion having a height which is gradually increased from a tip end of the cut out portion toward the distal end of the insertion section.

6. The intubation assistance instrument as claimed in claim 5, wherein the portion of the tip part of the outer wall part of the curved portion is formed into a shape having a rounded apex part when viewed from a side thereof.

7. The intubation assistance instrument as claimed in claim 1, wherein the insertion section has a bottom which defines a bottom surface of the groove, the bottom has a cross section having a substantially arc shape.

8. The intubation assistance instrument as claimed in claim 1, further comprising a regulator which regulates a protruding direction of the intubation tube when the intubation tube inserted into the groove is allowed to protrude from the distal end of the insertion section.

9. The intubation assistance instrument as claimed in claim 8, wherein the regulator is provided with a protrusion formed on the inner surface of the outer wall part to protrude into the groove.

10. The intubation assistance instrument as claimed in claim 1, wherein a length of the cut out portion from its base end to the tip end is 50 to 95% of the entire length of the insertion section at the side of the outer wall part.

11. The intubation assistance instrument as claimed in claim 1, wherein the intubation assistance instrument is configured to removably hold a curved intubation tube and guide the intubation tube into the trachea of the patient.

12. An intubation assistance apparatus, comprising the intubation assistance instrument of claim 1.

13. The intubation assistance apparatus as claimed in claim 12, further comprising a main body to which the intubation assistance instrument is removably mounted.

14. An intubation assistance instrument which is insertable into a trachea of a patient, the intubation assistance instrument comprising:

an insertion section having a straight portion with a tip part and a curved portion continuously extended from the tip part of the straight portion, the insertion section being formed with a groove along a longitudinal direction thereof, the curved portion having an inner wall part and an outer wall part which define the groove, and the outer wall part being formed with a cut out portion excluding a tip part of the curved portion, and wherein the tip part of the outer wall part of the curved portion has a portion having a height which is gradually increased from a tip end of the cut out portion toward the distal end of the insertion section.

15. An intubation assistance instrument which is insertable into a trachea of a patient, the intubation assistance instrument comprising:

an insertion section having a straight portion with a tip part and a curved portion continuously extended from the tip part of the straight portion, the insertion section being formed with a groove along a longitudinal direction thereof, the curved portion having an inner wall part and an outer wall part which define the groove, and the outer wall part being formed with a cut out portion excluding a tip part of the curved portion, and wherein a length of the cut out portion from its base end to the tip end is 50 to 95% of the entire length of the insertion section at the side of the outer wall part.

\* \* \* \* \*